US005897873A

United States Patent [19]

Popescu

[11] Patent Number: 5,897,873

[45] Date of Patent: Apr. 13, 1999

[54] AFFINITY ASSOCIATED VACCINE

[75] Inventor: Mircea Popescu, Plainsboro, N.J.

[73] Assignee: The Liposome Company, Inc., Princeton, N.J.

[21] Appl. No.: 08/392,676

[22] Filed: Feb. 23, 1995

Related U.S. Application Data

[63] Continuation-in-part of application No. 08/108,822, Aug. 18, 1993, and a continuation of application No. 08/146,463, Nov. 2, 1993, abandoned, which is a continuation of application No. 07/397,758, Aug. 23, 1989, abandoned, said application No. 08/108,822, is a continuation of application No. 07/758,587, Sep. 12, 1991, Pat. No. 5,288,499, which is a division of application No. 07/425,727, Oct. 23, 1989, Pat. No. 5,231,112, which is a continuation-in-part of application No. 06/773,429, Sep. 10, 1985, Pat. No. 4,891,208, which is a continuation-in-part of application No. 06/721,630, Apr. 10, 1985, Pat. No. 4,721,612, which is a continuation-in-part of application No. 06/599,691, Apr. 12, 1984, abandoned.

[51] Int. Cl.[6] .................... A61K 9/127

[52] U.S. Cl. .................... 424/450; 424/204.1; 424/206.1; 424/208.1

[58] Field of Search .................... 424/204.1, 206.1, 424/208.1, 229.1, 231.1, 812, 450

[56] References Cited

U.S. PATENT DOCUMENTS

| | | | |
|---|---|---|---|
| 4,053,585 | 10/1977 | Allison et al. | 424/92 |
| 4,148,876 | 4/1979 | Almeida et al. | 424/89 |
| 4,199,565 | 4/1980 | Fullerton | 424/89 |
| 4,522,803 | 6/1985 | Lenks et al. | 424/1.1 |
| 4,588,578 | 5/1986 | Fountain et al. | 424/1.1 |
| 4,663,161 | 5/1987 | Mannino et al. | 424/450 X |
| 4,721,612 | 1/1988 | Janoff et al. | 424/1.1 |
| 4,826,687 | 5/1989 | Nerome et al. | 424/450 |
| 5,026,557 | 6/1991 | Estis et al. | 424/450 |
| 5,049,386 | 9/1991 | Eppstein et al. | 424/427 |
| 5,100,662 | 3/1992 | Bolcsak et al. | 424/88 |

FOREIGN PATENT DOCUMENTS

| | | |
|---|---|---|
| 0 011 549 | 5/1980 | European Pat. Off. . |
| 0 047 480 | 3/1982 | European Pat. Off. . |
| 86/00238 | 1/1986 | WIPO . |
| 87/00043 | 1/1987 | WIPO . |
| 89/05633 | 6/1989 | WIPO . |

OTHER PUBLICATIONS

Alving, et al., *Vaccine*, 4:166–172, 1986.

Almeida, et al., "Formation of Virsomes from Influenza Subunits and Liposomes", 1975, The Lancet, 899–901.

Alving, Chapter 6 of Liposomes, Marcel Dekker, NY Marc Ostro, ed. pp. 195–218.

Bangham, et al., "Diffusion of Univalent Ions Across the Lamellae of Swollen Phospholipids,", 1965, J. Mol. Biol. 13:238–252.

Bormann, et al., "Synthetic peptides mimic the assembly of transmembrance glycoproteins", Chem. Abs. 110(23), 28025j.

Davis, et al., "Liposomes as adjuvants with immunopurified tetanus toxoid: the immune response", 1986/1987, Immunol. Let. 14:341–348.

Davis, et al., *Immunology*, 61:229–243, (1987).

Fauci, et al. "Development and Evaluation of a Vaccine for Human Immunodeficiency Virus (HIV) Infection", Annals of Internal Medicine, 110(5):373–385, 1989.

Fauci, et al. "The Development of an AIDS Vaccine: Progress and Promise", Public Health Report, 103(3):230–236, 1988.

Francis, et al., "Immunological Priming with Synthetic Peptides of Foot and Mouth Disease Virus", 1985, J. Gen. Virol. 66:2347–2354.

Gardner, et al., "Animal models of AIDS", FASEB J. 3:2593–2606, Dec. 1989.

Humphries, "Evidence for direct control of an in vitro plaque–forming cell response by quantitative properties of intect, fluid, haptenated liposomes: a potential model system for antigen presentation by macrophages", 1981, J. Immunol. 126(2):688–692.

Kraaijeveld, et al., "The effect of liposomal charge on the netralizing antibody response against inactivated encephalomyocarditis and Semliki Forest viruses", 1984, Clin. Immunol. 56:509–514.

Kramp, et al., "Liposomal Enhancement of the Immunogenicity of Adenovirus Type 5 Hexon and Fiber Vaccines", 1979, Infec. and Immun. 25(2):771–773.

Naylor, et al., "In Vivo Induction of Anti–Herpes Simplex Virus Immune Response by type 1 Antigens and Lipid A Incorporated into Liposomes", 1982, Infec. and Immun. 36(3):1209–1216.

Papahadjapoulos, et al., "Phospholipid Model Membranes I. Structural Characteristics of Hydrated Liquid Crystals," 1967 Biochim. Biophys. Acta, 135:624–638.

Pierce, et al., "Enhancement by lipid A of Mucosal Immunogenicity of Liposome–Associated Cholera Toxin", 1984, Rev. Infect. Dis. 6(4):563–566.

Putney, et al., "HTLV–III/LAV–Neutralizing Antibodies to an *E. coli*–Produced Fragment of the Virus Envelope", 1986, Science 234:1392–1395.

Siddiqui, et al., "Vaccination of Experimental Monkeys Against *Plasmodium falciparum:* A Possible Safe Adjuvant", 1978, Sci. 201:1237–1239.

Tan, et al., "Effect of interleukin–2 on the immunoadjuvant action of liposomes", 1989, Biochem. Soc. Trans. 17:693–694.

Tan, et al., "Incorporation of reconstituted influenza virus enveloped into liposomes studies of the immune response in mice", 1989, Biochem. Soc. Trans. 17:129–130.

(List continued on next page.)

*Primary Examiner*—Jose G. Dees
*Assistant Examiner*—Dameron Jones
*Attorney, Agent, or Firm*—Kenneth B. Rubin; Rosanne Goodman

[57] ABSTRACT

Disclosed is a vaccine against an infective agent, the vaccine comprising a liposome having an exterior and an interior and having externally disposed affinity associated antigen material of at least one, preferably nonpartitioning, antigen representative of said infective agent. Also disclosed is a method of preparation and use of this vaccine.

9 Claims, No Drawings

OTHER PUBLICATIONS van Houte, et al., "Characterization of immunogenic properties of haptenated liposomal model membranes in mice I. Thymus Independence of the Antigen", 1979, Immunol. 37:505–514.

van Houte, et al., "Characterization of immunogenic properties of haptenated liposomal model membranes in mice V. Effect of membrane Composition of Huymoral and Cellular Immunogenicity", 1981, Immunol 44:561–568.

van Rooijen, et al., "Liposomes in Immunology: Evidence that their adjuvant effect results from surface exposition of the antigens", 1980, Cell. Immunol, 49:402–407.

Walden, et al., "Induction of regulatory T–lymphocyte responses by liposomes carrying major histocompatibility complex molecules and foreign antigen":, 1985, Nature 315(23):327–329.

Yin, et al., "Effect of Various Adjuvants on the Antibody Response of Mice to Pheumococcal Polysaccharides", 1988, J. Biol. Res. Mod. 8:190–205.

94367959 Medline, "NIH Conference: HIV Vaccine Development: A Progress Report," Hoth et al., *Ann. Intern. Med.* 121(8)603–611, 1994.

90076756 Medline, "Animal Models of AIDS" Gardner et al., *FASEB J.* 3(14) 2593–609 (1989).

89133269 Medline "NIH Conference . . . " Fauci et al., *Ann. Intern. Med.* 110(5) 373–85 (1989).

88234863 Medline, "The development of an AIDS vaccine" . . , Public Health Rep, 103(3) 230–6 (1988).

Davis et al., *Immunology*, vol. 61, pp. 229–234 (1987).

Alving et al., *Vaccine*, vol. 4, pp. 166–172, 1986.

Kinsky et al., *J. of Immunol. Methods*, vol. 65, pp. 295–306, 1983.

AFFINITY ASSOCIATED VACCINE

This application is a continuation-in-part of U.S. Ser. No. 08/108,822, filed Aug. 18, 1993, which is a continuation of U.S. Ser. No. 07/758,587, filed Sep. 12, 1991 and now U.S. Pat. No. 5,288,499, which is a division of U.S. Ser. No. 07/425,727, filed Oct. 23, 1989 and now U.S. Pat. No. 5,231,112, which-in-turn is a continuation-in-part of U.S. Ser. No. 06/773,429, filed Sep. 10, 1985 and now U.S. Pat. No. 4,891,208, which is a continuation-in-part of U.S. Ser. No. 06/721,630, filed Apr. 10, 1985 and now U.S. Pat. No. 4,721,612, which is a continuation-in-part of U.S. Ser. No. 06/599,691, filed Apr. 12, 1984 and now abandoned. This application is also a continuation of U.S. Ser. No. 08/146,463, filed Nov. 2, 1993 and now abandoned, which is a continuation of U.S. Ser. No. 07/397,758, filed Aug. 23, 1989 and now abandoned.

FIELD OF THE INVENTION

This invention concerns a vaccine against an infective agent, the vaccine comprising a liposome having an exterior and an interior and having externally disposed affinity (noncovalently) associated antigen material of at least one, preferably nonpartitioning, antigen representative of said infective agent. Also disclosed is a method of preparation and use of this vaccine.

BACKGROUND OF THE INVENTION

In the vaccine art antigens are introduced into an organism in a manner so as to stimulate an immune response in the host organism. The induction of an immune response depends on many factors among which are believed to be the chemical composition and configuration of the antigen, the potential of the immune system of the challenged organism, and the manner and period of administration of the antigen. An immune response has many aspects some of which are exhibited by the cells of the immune system, (e.g., B-lymphocytes, T-lymphocytes, macrophages, and plasma cells). Immune system cells may participate in the immune response through interaction with antigen, interaction with other cells of the immune system, the release of cytokines and reactivity to those cytokines. Immune response is conveniently (but arbitrarily) divided into two main categories—humoral and cell-mediated. The humoral component of the immune response includes production of immunoglobulins specific for the antigen. The cell-mediated component includes the generation of delayed-type hypersensitivity and cytotoxic effector cells against the antigen.

In some instances immune response is the result of an initial or priming dose of an antigen that is followed by one or more booster exposures to the antigen. Priming with relatively strong immunogens and liposomes is discussed in "Liposomal Enhancement of the Immunogenicity of Adenovirus Type 5 Hexon and Fiber Vaccines", Kramp, W. J. et al., *Infection and Immunity,* 25:771–773 (1979) and "Liposomes as Adjuvants with Immunopurified Tetanus Toxoid: the Immune Response", Davis, D. et al., *Immunology Letters,* 14:341–8 (1986/1987).

Ideally, an antigen will exhibit two properties, the capacity to stimulate the formation of the corresponding antibodies and the propensity to react specifically with these antibodies. Antigens bear one or more epitopes which are the smallest part of an antigen recognizable by the combining site of an antibody.

In particular instances antigens or fractions antigens with particular presenting conditions, the immune response precipitated by the desired antigen is inadequate or nonexistent and insufficient immunity is produced. This is particularly the case with peptides or other small molecules used as antigens.

In such cases the vaccine art recognizes the use of substances called adjuvants to potentiate an immune response when used in conjunction with an antigen or immunogen. Adjuvants are further used to an elicit immune response sooner, or a greater response, or with less antigen or immunogen or to increase production of certain antibody subclasses that afford immunological protection, or to enhance components of the immune response (e.g., humoral, cellular). Liposomal vaccines and adjuvancy are further discussed in U.S. patent application Ser. No. 07/397,777, now abandoned, to Popescu et al., filed on date even herewith the teachings of which are incorporated herein by reference.

Known adjuvants are Freund's Adjuvants (and other oil emulsions Bortedella Pertussis, Lipid A (the glycophospholipid moiety of lipopolysaccharide found in Gram-negative bacteria), aluminum salts (and other metal salts), Mycobacterial products (including muramyl dipeptides), and liposomes. As used herein the term "adjuvant" will be understood to mean a substance or material administered together or in conjunction with an antigen which increases the immune response to that antigen. Adjuvants may be in a number of forms including emulsion (e.g., Freund's adjuvant) gels (aluminum hydroxide gel) and particles (liposomes) or as a solid material.

It is believed that adjuvant activity can be affected by a number of factors. Among such factors are (a) carrier effect, (b) depot formation, (c) altered lymphocyte recirculation, (d) stimulation of T-lymphocytes, (e) direct stimulation of B-lymphocytes and (f) stimulation of macrophages.

With many adjuvants adverse reactions are seen. In some instances adverse reactions include granuloma formation at the site of injection, severe inflammation at the site of injection, pyrogenicity, adjuvant induced arthritis or other autoimmune response, or oncogenic response. Such reactions have hampered the use of adjuvants such as Freund's adjuvant.

In particular embodiments liposome adjuvants are utilized. U.S. Pat. No. 4,053,585 issued Oct. 17, 1977 to Allison et al. states that liposomes of a particular charge are adjuvants.

Other substances such as immunomodulators (e.g., cytokines such as the interleukins) may be combined in adjuvants as well.

Humoral immune response may be measured by many well known methods. Single Radial Immunodifussion Assay (SRID), Enzyme Immunoassay (EIA) and Hemagglutination Inhibition Assay (HAI) are but a few of the commonly used assays.

EIA, also known as ELISA (Enzyme Linked Immunoassay), is used to determine total antibodies in a sample. The antigen is adsorbed to the surface of a microtiter plate. The test serum is exposed to the plate followed by an enzyme linked immunogloublin, such as IgG. The enzyme activity adherent to the plate is quantified by any convenient means such as spectrophotometry and is proportional to the concentration of antibody directed against the antigen present in the test sample.

Tests to measure cellular immune response include determination of delayed-type hypersensitivity or measuring the proliferative response of lymphocytes to target antigen.

Liposomes are completely closed lipid bilayer membranes containing an entrapped aqueous volume. Liposomes may be unilamellar vesicles (possessing a single bilayer membrane) or multilameller vesicles (onion-like structures characterized by multiple membrane bilayers, each separated from the next by an aqueous layer). The bilayer is composed of two lipid monolayers having a hydrophobic "tail" region and a hydrophilic "heads" region. The structure of the membrane bilayer is such that the hydrophobic (nonpolar) "tails" of the lipid monolayers orient toward the center of the bilayer while the hydrophilic "head" orient towards the aqueous phase.

The original liposome preparation of Bangham, et al. (*J. Mol. Biol.,* 1965, 13:238–252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (*Biochim. Biophys. Acta.,* 1968, 135:624–638), and large unilamellar vesicles.

Unilamellar vesicles may be produced using an extrusion apparatus by a method described in Cullis et al., PCT Application No. WO 86/00238, published Jan. 16, 1986, entitled "Extrusion Technique for Producing Unilamellar Vesicles" incorporated herein by reference. Vesicles made by this technique, called LUVETS, are extruded under pressure once or a number of times through a membrane filter. LUVETs will be understood to be included in the term "unilamellar vesicle".

Another class of liposomes are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles (MPVs) as described in U.S. Pat. No. 4,588,578 to Fountain, et al. and frozen and thawed multilamellar vesicles (FATMLV) wherein the vesicles are exposed to at least one freeze and thaw cycle, as described in Bally et al., PCT Publication No. 87/00043, Jan. 15, 1987, entitled "Multilamellar Liposomes Having Improved Trapping Efficiencies" corresponding to U.S. Pat. No. 4,975,282. U.S. Pat. No. 4,721,612 to Janoff et al. describes steroidal liposomes for a variety of uses. The teachings of these references as to the preparation and use of liposomes are incorporated herein by reference.

Lipids of net negative charge are well known in the art and include for example, phosphatidyserine, phosphatidic acid, and phosphatidylglycerol. Lipids of net positive charge are well known in the art and include for example, aminodiglycerides, glyceridecholine, stearylamine, trimethylstearylamine, and dioctadecyl trimethylamonnio propane. In general any bilayer forming amphiphile which has a charged hydrophilic moiety may be used.

In addition, lipid charge may be manipulated by a number of methods well known in the art, such as by linking the lipid to a moiety of appropriate net charge. For example, the neutral lipid cholesterol may be linked to succinic acid (negative charge) to yield cholesterol hemisuccinate (CHS) of negative charge. The tris(hydroxymethyl)aminomethane form of CHS is designated $CHS_{tris}$ its application to liposomes is more fully discussed in U.S. Pat. No. 4,721,612 the teachings of which are incorporated herein by reference.

SUMMARY OF THE INVENTION

This invention includes a composition comprising a liposome in noncovalent association with an externally disposed antigen and in one embodiment further comprising adjuvant or further comprising aluminum hydroxide or Lipid A. Preferred antigens are nonpartitioning. In some embodiments the antigen is hydrophilic or lipophilic. Variously the affinity association is noncovalent association and the like such as electrostatic, hydrophilic, hydrogen bonding, or other bonding related to van der Waals forces such as configurational stickiness. Liposomes of this invention may be unilamellar or multilamellar.

In particular applications liposomes may comprise cholesterol hemisuccinate, phosphatidylserine, phosphatidic acid, or phosphatidylglycerol as well as aminodiglyceride, glyceridecholine, stearylamine, trimethylstearylamine, dioctadecyl trimethylammonio derivatives (e.g., 1,2 bis (oleoyloxy)-3-dioctadecyl trimethylammonio propane—"DOTAP") or any bilayer forming amphiphile having a charged hydrophilic moiety.

Useful antigens include HIV or a portion thereof with particular reference to PB1, antigen include peptides, glycopeptides or glycoproteins. In particular applications the antigen is influenza or fragments thereof, herpes or fragments thereof, haemophilus B or fragments thereof or malaria or fragments thereof. Antigens also include isolated or bioengineered fragments of viruses, bacteria, cancer cells, humoral cells and body fluid components.

In another embodiment the invention includes a method of producing a vaccine composition comprising a liposome in affinity (noncovalent) association with a externally disposed and preferably nonpartitioning antigen. This method comprises contacting in an aqueous solution, an antigen and a liposome comprising said bilayer forming material of reciprocal affinity to said antigen, such that the antigen and the liposome forms an affinity association. Optionally, the process may further include removing non-affinity associated antigen.

In the practice of this method the affinity between antigen and liposome is electrostatic or hydrogen bonding or is configurational stickiness. Additionally by this method the liposome is of net negative charge and the antigen of net positive charge or the liposome is of net positive charge and the antigen of net negative charge. In the practice of this method in one embodiment the liposome comprises CHS. In another embodiment the antigen comprises PB1. In particular applications the liposomes are subjected to shearing force.

This invention yet further includes a method of inducing an immune response in an animal, including a human, comprising administering to said animal a therapeutically effective amount of a composition comprising a liposome in noncovalent affinity association with an externally disposed preferably nonpartitioning antigen. The method can further utilize adjuvant such as aluminum hydroxide or Lipid A. Variously by this method antigen is hydrophilic or lipophilic. Further by this method the affinity is electrostatic, hydrogen bonding or configurational stickiness.

In the practice of this method of treatment in various embodiments the liposome comprises cholesterol hemisuccinate, phosphatidylserine, phosphatidic acid, or phosphatidylglycerol as well as aminodiglyceride, glyceridecholine, stearylamine, trimethylstearylamine, or dioctadecyl trimethylammonio derivatives or any bilayer forming amphiphile having a charged hydrophilic moiety. Antigens can comprise HIV or a portion thereof, particularly PB1. Variously antigens are noted to be proteins, peptides, glycopeptides, or glycoproteins, polypeptides, or poly (amino acid) and will be termed, collectively, "peptide".

Particularly noted as antigens are influenza or fragments thereof, herpes or fragments thereof, haemophilus B or fragments thereof, or malaria or fragments thereof, as well as isolated or bioengineered fragments of viruses, bacteria, cancer cells, humoral cells and body fluid components.

DETAILED DESCRIPTION OF THE INVENTION

For clarity, in the discussion of this invention the following definitions will be used:

"Adjuvant" shall mean a substance or material to potentiate an immune response when used in conjunction with an antigen or immunogen. Adjuvants are further used to elicit an immune response sooner, or a greater response, or with less antigen.

"Antigen" shall mean a substance or material that is recognized specifically by an antibody and/or combines with an antibody. Particular note is made of both natural and bioengineered antigens such as peptides, glycopeptides and glycoproteins. Specific antigens include antivirals such as herpes, hepatitis, rabies, parainfluenza, measles, mumps, respiratory syncytial virus; antibacterials such as pneumonia, haemophilis B, staphylococcus, meningococcus, Neisseria gonorrhea; and protozoa such as malaria or fragments thereof.

"Epitope" shall mean the smallest part of an antigen recognizable by the combining site of an immunoglobulin.

"Externally disposed" shall, in referring to antigen or immunogen, mean, positioned by an "affinity association" so as to bear an epitope external to the outermost lamella of an associated liposome. Included are epitopes tonically associated with the liposome, nonpartitioned into the outermost lamellae, and with epitope exposed.

"Affinity association" shall mean noncovalent intermolecular associations such as electrostatic association, hydrogen bonding, and configurational stickiness.

"Configurational stickiness" shall be understood to mean physical parameters that facilitate immobilization of antigen or immunogen externally on a liposome such as van der Waals forces.

"Nonpartitioning" refers to antigen or immunogen refers to hydrophilic immunogens and those lipophilic immunogens the epitopes of which are not substantially incorporated into the outermost lamella of a liposome. Those lipophilic immunogens that can be separated from liposomes by physical manipulation such as by dialysis, charge manipulation or other equilibrium based separations are deemed to be not substantially incorporated into the lamellae and nonpartitioning.

"Immune response" shall mean a specific response of the immune system of an animal to antigen or immunogen. Immune response may include the production of antibodies.

"Immunity" shall mean a state of resistance of a subject animal to an infecting organism or substance. It will be understood that infecting organism or substance is defined broadly and includes parasites, toxic substances, cancers and cells as well as bacteria and viruses. A Therapeutically Effective Immunization Course will produce immune response to protect the organism against challenging antigen.

"Immunization conditions" shall mean factors which affect an immune response including the amount and kind of antigen or adjuvant delivered to a subject animal, method of delivery, number of inoculations, interval of inoculation, the type of subject animal and its presenting condition.

"Immunization dose" shall mean the amount of antigen or immunogen needed to precipitate an immune response. This amount will vary with the presence and effectiveness of various adjuvants. This amount will vary with the animal and immunogen or antigen or adjuvant but will generally be between about 0.1 ug/ml or less to about 500 ug per inoculation. The immunization dose is easily determined by methods well known to those skilled in the art, such as by conducting statistically valid host animal immunization and challenge studies. See, for example, *Manual of Clinical Immunology*, H. R. Rose and H. Friedman, American Society for Microbiology, Washington, D.C. (1980). In some instances several immunization doses including booster doses will be administered to provide immunity.

"Immunogen" shall mean a substance or material (including antigens) that is able to induce an immune response alone or in conjunction with an adjuvant. This will generally be a protein, peptide, polysaccharide, nucleoprotein, lipoprotein, synthetic polypeptide, or hapten linked to a protein, peptide, polysaccharide, nucleoprotein, lipoprotein or synthetic polypeptide or other bacterial, viral or protozoal fractions. It will be understood that "immunogen" includes substances which do not generate an immune response (or generate only a therapeutically ineffective immune response) unless associated with an adjuvant (e.g., small peptides) which will be referred to as "adjuvant-obligatory" immunogens.

"Infective agent" shall mean a disease causing agent including fungi, bacteria, viruses and parasites.

"Mimetic", in relation to antigens, immunogens and epitopes, refer to a moiety (either natural or synthetic) that duplicates by structure, accessibility or reactivity the response of B-cell immuno-receptors to the subject antigen in native state configuration or epitope in native state configuration.

"Native state configuration" shall mean that organization of a moiety as it is when present in situ in its usual condition, to be distinguished from non-native state configuration (denatured) wherein the moiety is altered as to immunoreactivity from that of the in situ organization.

"Vaccine" shall mean a pharmaceutical formulation which induces an immune response or immunity in a subject animal.

Antigens or immunogens may have a net positive or negative charge, or may be neutral. The net charges are easily determined by a number of techniques well known in the art. For peptides the net charge may be assessed through determination of the isoelectric point. Peptides of isoelectric points of about 5 or less have net negative charge and the peptides are soluble in basic solution. Isoelectric points of about 8 or more indicate a net positive charge and the peptides are soluble in acid solution. Isoelectric points from 5 to 8 indicate generally neutral peptides (from slightly acidic to slightly basic). The determination of isoelectric points is well known in the art and is discussed in "Relationship Between in vivo Degradative Rates and Isoelectric Points of Proteins", Dice, et al., *Proc. Natl. Acad. Sci. USA,* 72:3895–97 (1975) the teachings of which are incorporated herein by reference.

Net charges on peptides can be manipulated by a number of methods well known in the art including adding charge bearing amino acids or amino acid segments. By way of example lysine and arginine add positive charge while aspartic and glutamic acid add negative charge. It is important to note in any manipulation of antigens or immunogens including addition of amino acids or exposure to acidic or basic solutions or temperature variation or light that conditions must not be such as to compromise immunogenicity or native state configuration.

A particularly useful immunogen is the PB1 fraction of the HIV 1 virus (Repligen Corporation, Cambridge, Mass.). This fraction is characterized in "HTLV-III/LAV-Neutralizing Antibodies of an *E. coli*-Produced Fragment of the Virus Envelope", Putney, et al., *Science,* 234:1392–5 (1986) the teachings of which are incorporated herein by reference. PB1 peptide is soluble in aqueous solution containing solubilizing substances such as urea and detergents and was supplied in such solution. Such solubilization substances were incompatible with pharmaceutical preparations and a dialysis process was utilized to remove them.

Antigens or immunogens which partition into the liposome lamellae such as melanoma antigen in CHS liposomes may not yield a sufficient immunogenic response without repeated inoculation and additional adjuvant. Without being bound by any particular theory it is believed that this partitioning results in the limitation of exposure of epitopes externally to the adjuvant liposomes. Modification (e.g., conjugation with a nonpartitioning moiety) of such an antigen or immunogen while preserving native state configuration acts so as to prevent partitioning. In addition it can be advantageous to utilize both affinity associated antigen and entrapped antigen in a particular composition, vaccine or dosage form.

A preferred vaccine of this invention is a liposome organized so as to have an immunogen in electrostatic association with the exterior of said liposome. The preferred liposome may be multilamellar (e.g., multilamellar vesicles or stable plurilamellar vesicles). In a particular embodiment the vaccine contains externally disposed antigen or immunogen in such electrostatic association.

In some embodiments the most successful immunogens will be those purified from (or duplicative or mimetic of) the infective agent while maintaining immunogen native state configuration. It is understood that some vaccines are prepared without resort to living infective organisms due to the potential for contamination of the final vaccine. It is thus useful to produce immunogens synthetically (including bioengineering) such as through techniques of recombinant DNA technology, recombinant RNA technology or other synthesis in host cells, but it is preferable that even synthetically produced immunogens be of native state configuration.

Selection of lipid and antigen of reciprocal affinity is simply accomplished by those skilled in the art. Depending upon the type of noncovalent affinity association applicable various association techniques are used. For hydrogen bonding the elevation of temperature of the aqueous solution suspending antigen and liposomes above the transition temperature of the affinity bonded entities is effective. For van der Waals, or electrostatic or configurational stickiness admixing of the antigen and liposomes in aqueous solution is sufficient, but as to electrostatic affinity the liposome and antigen are of opposite charge.

Degree of affinity association of nonpartitioning antigen or immunogen is simply determined by methods well known in the art. By one method the relative attachment and nonattachment is determined by centrifuging the liposomes and antigen or immunogen admixture and then determining the amount of antigen or immunogen in the supernatant. The amount not in the supernatant is a measure of the amount affinity attached.

Also useful is priming in generation of the immune response. A vaccine may generate a weak immune response that is not greatly potentiated on secondary challenge. However, after a first administration of the adjuvant-associated immunogen, a substantial immune response is generated upon application of a second inoculation of the adjuvant free immunogen in solution.

The efficacy and utility of this invention is disclosed in Tables 1 and 2.

Table 1 presents the data of an experiment in which a $CHS_{tris}$ formulation was compared with other liposome formulations.

Liposomes made of $CHS_{tris}$ (Table 1, group F) were prepared by the multilamellar vesicles (MLV) procedure. This formulation involves the coating of the surface of negatively charged liposomes with the positively charged antigen.

Liposomes made of dimyristoylphosphatidylcholine/cholesterol (DMPC/CHOL) were prepared using either stable plurilamellar vesicle (SPLV) procedure (D–W, D) or monophasic vesicle (MPV) procedure (D–E, D–T).

A. SPLV Liposome D–W

DMPC (80 mg) and cholesterol (20 mg) in 1 ml chloroform were rotoevaporated under vacuum to a dry film and further solubilized in 5 ml ether+0.5 ml ethanol at 40° C. for a few seconds until the solution was clear. The PB1 antigen (100 ug) in 0.5 ml 1% acetic acid was added to this solution and the resulting mixture was sonicated under a stream of $N_2$ at 40° C. for about 1 minute until dryness (2–3 minutes). The resulting dry material was resuspended in 10 ml phosphate buffered saline minus $Ca^{++}$ and $Mg^{++}$ (KCl 2 g/L, $KH_2PO_4$2 g/L, NaCL 80 g/L, $NaPO_47H_2O$ 21.6 g/L) ("PBS minus") to a milky suspension which was then centrifuged at 10,000 rpm for 10 minutes at 4° C. The pellet of liposomes was resuspended in 2 ml PBS minus to a final concentration of 50 mg lipid/ml.

B. SPLV, Liposome D

This liposome was prepared as described above for the D–W liposome except that the centrifugation step was omitted. Subsequently the material dried by $N_2$ stream was resuspended in 2 ml PBS minus to a final concentration of 50 mg lipid and 50 ug antigen/ml.

C. MPV, Liposome D–E

Cholesterol (20 mg) was dissolved in 1 ml ethanol containing 80 mg solubilized DMPC by brief heating to 40° C. (10–20 sec.) and stirring. The solution of antigen (1 ml) was prepared separately by mixing 100 ug PB1 in 0.13 ml 1% acetic acid and 0.87 ml ethanol and immediately mixed with the lipid solution. The mixture was rotoevaporated under vacuum at 40° C. and the resulting material was resuspended in 2 ml PBS minus by sonication for 10 seconds at 40° C. to a final suspension of 50 mg lipid and 50 ug antigen/ml.

D. MPV, Liposome D–T

This liposome was prepared as described above for the D–E liposome except that the ethanol was replaced by Tert-butyl-alcohol (TBA).

E. Liposome, H–D mixture

This preparation was done by mixing 0.5 ml of SPLV, liposome D made of DMPC/CHOL and 0.5 ml of empty MLV liposome H made of $CHS_{tris}$ as described below. The mixture contained 75 mg lipids (50 mg $CHS_{tris}$, 25 mg DMPC/CHOL) and 25 ug PB1 antigen/ml.

F. MLV, Liposome H

Empty $CHS_{tris}$ liposomes were prepared by hydration of 100 mg $CHS_{tris}$ with 1 ml of PBS minus for 2 hr. at room temperature and intermittent vigorous vortex-mixing. Separately, a fresh dialysate of PB1 antigen in 1% acetic acid was diluted in PBS minus at 100 ug antigen/ml and 0.5 ml of this solution was immediately mixed with 0.5 ml of empty $CHS_{tris}$ liposomes to allow affinity association between vesicles and antigen. The mixture contained 50 mg lipid and 50 ug antigen/ml.

G. Control of Complete Freund Adjuvant (CFA) and dialyzed (d) antigen

Equal 1 ml volumes of complete Freund's adjuvant (CFA) in oil and PB1 dialyzed against 1% acetic acid and further diluted in 1% acetic acid to 100 ug antigen/ml, were mixed thoroughly and emulsified by repeated passage through a 16 G needle connecting two 5 ml syringes. This emulsion contained 50 ug antigen/ml.

H. Control of CFA and non-dialyzed antigen

This emulsion was prepared as described above except that PB1 antigen was not dialyzed.

I. Control of non-dialyzed antigen in solution

PB1 at a concentration of 0.77 mg/ml in a 50 mM phosphate buffer, pH 6.8, containing 2 mM EDTA, 10 mM DTT and 8M urea was diluted in PBS minus to 50 ug/ml.

J. Control of dialyzed antigen in solution

Stock PB1 solution (0.77 mg/ml in a 50 mM phosphate buffer, pH 6.8, containing 2 mM EDTA, 10 mM dithiothreitol and 8 m urea) was dialyzed against 1% acetic acid (pH 2.5) and the dialyzed antigen diluted before use in PBS minus at 50 ug/ml.

Immunization

Balb/C (Jackson), 6–8 weeks old female mice were inoculated intramuscularly ("IM") at day 0, 15, 35 and blood was taken at day 0, 14, 28, 49, 63 and 79. The dose of antigen was 5 ug/0.1 ml/inoculum except group E which received 2.5 ug.

Determination of humoral immune response

PB1 specific antibody (IgG and IgM) was determined by a standard ELISA procedure.

Data presented in Table 1 indicated that the adjuvant effect provided by CHS liposomes with affinity associated immunogen (group F) was similar with that provided by complete Freund's adjuvant "CFA" (groups G and H), a potent but highly toxic adjuvant.

Out of six liposomal formulations, five induced a positive response in all mice tested 49 days or more after primary inoculation, indicating an enhancement by liposomes of the secondary IgG memory response and involvement of helper T-cells. The magnitude of the response, however, was highly dependent on the nature of liposome formulation and varied from low (groups A, B, C), to medium (group E) to high (group F).

Since the dose of antigen in group E was 2.5 ug/0.1 ml/inoculum (rather than 5 ug) the adjuvant effect provided by this formulation was probably underestimated. Both the original and acid dialyzed PB1 in PBS minus were weak immunogens (group I and J). In contrast, the CHS liposome affinity associated preparation (group F) induced a high antibody response and in addition no or minimal reaction was observed at the site of inoculation.

TABLE 2

In order to compare the effect of CHS affinity associated liposomes with that of Alum, a standard adjuvant used in vaccines for humans, groups of five mice were immunized with 20, 5, 1.25 and 0.31 ug PB1 in either Alum or CHS formulation.

The amount of Alum was kept constant at 0.4 mg/ml of physiological saline (USP). The CHS liposome-PB1 formulations were prepared as described previously (group F, table 3). A formulation containing 50 ug antigen/ml was further diluted in a suspension of empty CHS liposomes in PBS minus such that the amount of lipids was kept constant at 50 mg/ml and the antigen decreased to 2.5, 1.25 and 0.31 ug/ml. Another CHS formulation at 50 mg lipid and 20 ug antigen was subjected to shearing force via vortexing and sonicating at low energy intermittently for 2 hours at room temperature in order to achieve a suitable suspension.

The results (Table 2) indicated that the CHS liposome with affinity associated immunogen was a much stronger adjuvant than Alum. The difference in immune titers were in general higher than one order of magnitude with the exception of lowest dose (0.31 ug PB1) in which the response remained low.

In addition, the comparison between CHS formulation and CFA formulation both at 1.25 ug antigen reinforced the conclusion of the previous experiment (Table 1) indicating a higher antibody response by CHS affinity associated liposomes than by CFA.

Vaccines are conveniently administered in a dosage form. A "dosage form" will be understood to mean any pharmaceutically form of administering a vaccine including subcutaneous, oral, intramuscular, and ocular administration and utilizing vaccines in live, attenuated or synthetic or bioengineered or partial forms along with adjuvants and optionally immunomodulators such as cytokines. The combinations of the foregoing elements are prepared so that the dosage form is adapted to produce a therapeutically effective immune response in the subject animal including a human as easily and effectively as possible.

The dosage forms including liposomal dosage forms resulting from the method of the present invention can be used therapeutically in mammals, including a human, in the treatment of infections or conditions which require the delivery of immunogens in its bioactive form. Such conditions include but are not limited to disease states such as those that can be treated or prevented with vaccines.

Dosage forms also include use of adjuvant as well as vaccine incorporated into gels such as aluminum gels, lipids such as Lipid A, liquid crystals, powders, precipitates and solutions. In particular embodiments the dosage form can be a unit dosage form configured and adapted to a single administration.

The mode of administration of the dosage form may determine the sites and cells in the organism to which the dosage form will be delivered. The dosage forms including liposomal dosage forms of the present invention can be administered alone but will generally be administered in admixture with a pharmaceutical carrier selected with regard to the intended route of administration and standard pharmaceutical practice. The dosage forms may be injected intramuscularly, subcutaneously or intradermally. The dosage forms may also be administered via oral routes. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art.

For administration to humans in the preventive or curative treatment of disease states responding to vaccine based therapy, the prescribing physician will ultimately determine the appropriate therapeutically effective dosage for a given human subject, and this can be expected to vary according to the age, weight, and response of the individual as well as the nature and severity of the patient's disease.

EXAMPLE 1

Affinity Attachment of Antigen to Liposome

PB1 is a positively charged peptide and thus dialysis of PB1 from stock solution was performed against a 1% acetic acid at a pH of 2.5. Upon dialysis the PB1 remained soluble for several hours in 1% acetic acid. It was noted that, were the pH to approach neutral pH, the PB1 antigen would rapidly precipitate. Affinity attachment of the PB1 to liposomes was accomplished by utilizing a liposome of reciprocal (here negative) charge. $CHS_{tris}$ liposomes having a negative charge were used, suspended in neutral (pH 7.2) buffer and then mixed with the PB1 in 1% acetic acid solution. Care was taken to avoid $CHS_{tris}$ precipitation as $CHS_{tris}$ liposome suspensions are rapidly precipitated by solutions below about pH 5. Therefore in order to maintain the integrity of the liposome suspension, upon addition of the PB1 in acetic acid solution, pH of the mixture was maintained above 5. Affinity association occured upon mixing of liposomes and antigen.

TABLE 1

SERUM ANTIBODY TITERS AFTER IMMUNIZATION OF BALB/C MICE WITH LIPOSOMAL PB1 FORMULATIONS

| Group and Formulation | Geometric Mean Titer (EIA Units/ml) Day 14 | Day 28 | Day 49 | Day 63 | Day 79 |
|---|---|---|---|---|---|
| A. Liposome D-W | — (0/5)[a] | — (0/5) | 66.08 (5/5) | 140.85 (5/5) | 74.00 (4/5) |
| B. Liposome D | — (0/5) | — (0/5) | 144.47 (5/5) | 95.68 (5/5) | 70.77 (4/5) |
| C. Liposome D-E | — (0/5) | 64.62 (4/5) | 113.00 (5/5) | 154.21 (4/4) | 180.90 (4/4) |
| D. Liposome D-T | — (0/5) | — (0/5) | — (0/5) | 35.00 (1/5) | — (0/5) |
| E. Liposome H-D | — (0/5) | 20.49 (4/5) | 663.15 (5/5) | 640.55 (4/4) | 618.41 (4/4) |
| F. Liposome H | — (0/5) | 1,135.78 (5/5) | 6,593.49 (4/4) | >11,465.31 (4/4) | 6,104.65 (3/3) |
| G. CFA-PB1 | — (0/5) | 1,138.58 (5/5) | >11,329.05 (5/5) | >11,465.31 (4/4) | 14,610.05 (4/4) |
| H. CFA-PB1 | — (0/5) | 321.03 (5/5) | 2,253.23 (5/5) | 2,875.41 (5/5) | 3,134.13 (5/5) |
| I. PB1 | — (0/5) | — (0/5) | 300.00 (1/5) | 43.47 (2/5) | — (0/4) |
| J. PB1 | — (0/5) | — (0/5) | 54.77 (2/5) | 94.87 (2/5) | 60 (1/4) |

[a]Number of responding mice per group. Mean titer was calculated from the individual titers of the responding mice only.

TABLE 2

SERUM ANTIBODY TITERS AFTER IMMUNIZATION OF BALB/C MICE WITH VARIOUS DOSES OF PB1 IN LIPOSOMAL AND ALUM FORMULATIONS

| Formulation | Dose (ug) | Geometric Mean Titer (EIA Units/ml) Day 14 | Day 28 | Day 49 |
|---|---|---|---|---|
| Alum | 20.0 | — (0/4)[a] | 161.34 (4/4) | 1,212.31 (4/4) |
| Liposome | 20.0 | 21.79 (2/4) | 2,411.18 (4/4) | 4,355.87 (4/4) |
| Alum | 5.0 | — (0/4) | 77.31 (5/5) | 349.27 (5/5) |
| Liposome | 5.0 | 38.73 (2/5) | 931.97 (5/5) | 7,949.76 (5/5) |

TABLE 2-continued

SERUM ANTIBODY TITERS AFTER IMMUNIZATION OF BALB/C MICE WITH VARIOUS DOSES OF PB1 IN LIPOSOMAL AND ALUM FORMULATIONS

| Formulation | Dose (ug) | Geometric Mean Titer (EIA Units/ml) Day 14 | Day 28 | Day 49 |
|---|---|---|---|---|
| Alum | 1.25 | — (0/5) | — (0/5) | 79.06 (2/5) |
| Liposome | 1.25 | — (0/5) | 152.02 (4/5) | 917.78 (4/5) |
| Control (PB1) | 1.25 | — (0/5) | — (0/5) | — (0/5) |
| Control (CFA) | 1.25 | — (0/5) | 38.91 (4/5) | 365.73 (5/5) |
| Alum | 0.31 | — (0/5) | 27.00 (1/5) | 30.00 (1/5) |
| Liposome | 0.31 | — (0/5) | — (0/5) | 42.17 (3/5) |

[a]Number of responding mice per group. Mean titer was calculated from the individual titers of the responding mice only.

I claim:

1. A composition which comprises:

(i) an adjuvant liposome which comprises a lipid consisting essentially of a cholesteryl hemisuccinate salt; and (ii) a peptide antigen in electrostatic association with the lipid wherein the peptide antigen has an isoelectric point of at least about 8 and is associated with the external surface of the liposome.

2. The composition of claim 1, wherein the antigen is a viral, bacterial, protozoal or cellular antigen.

3. The composition of claim 2, wherein the antigen is selected from the group consisting of human immunodeficiency virus and Haemophilus influenza B antigens.

4. The composition of claim 3, wherein the antigen is a human immunodeficiency virus antigen.

5. The composition of claim 1, wherein the cholesteryl hemisuccinate salt is a tris(hydroxymethyl)aminomethane salt.

6. The composition of claim 1 comprising an additional adjuvant.

7. The composition of claim 6, wherein the additional adjuvant comprises aluminum hydroxide.

8. A method of enhancing the immune response of an animal to a peptide antigen which comprises administering the composition of claim 1 to the animal.

9. A composition which comprises:

(i) an adjuvant liposome comprising a lipid which consists essentially of the salt form of an organic acid derivative of a sterol; and (ii) a peptide antigen having an isoelectric point of about 8, wherein the peptide antigen is electrostatically associated with the external surface of the liposome.

* * * * *